(12) United States Patent
Schiller

(10) Patent No.: US 7,344,517 B2
(45) Date of Patent: Mar. 18, 2008

(54) SYRINGE HAVING A RETRACTABLE NEEDLE

(75) Inventor: Eric Schiller, Kinnelon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 491 days.

(21) Appl. No.: 10/760,891

(22) Filed: Jan. 20, 2004

(65) Prior Publication Data

US 2005/0159707 A1 Jul. 21, 2005

(51) Int. Cl.
*A61M 5/00* (2006.01)
(52) U.S. Cl. ..................................... 604/110
(58) Field of Classification Search ................ 604/110, 604/218, 181, 187, 195, 198, 192, 222, 207, 604/263, 111; 128/919
See application file for complete search history.

(56) References Cited

U.S. PATENT DOCUMENTS

| | | | |
|---|---|---|---|
| 4,573,976 A | 3/1986 | Sampson | |
| 4,631,057 A | 12/1986 | Mitchell | |
| 4,737,144 A | 4/1988 | Choksi | |
| 4,747,831 A | 5/1988 | Kulli | |
| 4,795,432 A | 1/1989 | Karczmer | |
| 4,813,940 A | 3/1989 | Parry | |
| 4,985,021 A | 1/1991 | Straw | |
| 4,998,920 A | 3/1991 | Johnson | |
| 5,026,356 A | 6/1991 | Smith | |
| 5,053,018 A | 10/1991 | Talonn | |
| 5,061,251 A | 10/1991 | Juhasz | |
| 5,151,088 A | 9/1992 | Allison | |
| 5,156,599 A | 10/1992 | Ranford | |
| 5,163,918 A | 11/1992 | Righi | |
| 5,193,552 A | 3/1993 | Columbus | |
| 5,197,953 A | 3/1993 | Colonna | |
| 5,201,708 A | 4/1993 | Martin | |
| 5,217,437 A | 6/1993 | Talonn | |
| 5,242,420 A | 9/1993 | Martin | |
| 5,246,427 A | 9/1993 | Sturman | |
| 5,300,040 A | 4/1994 | Martin | |
| 5,304,149 A | 4/1994 | Morigi | |

(Continued)

FOREIGN PATENT DOCUMENTS

EP 0 307 367 A1 6/1992

(Continued)

*Primary Examiner*—Matthew F. DeSanto
(74) *Attorney, Agent, or Firm*—David M. Fortunato; Cohen, Pontani, Liberman & Pavane LLP

(57) ABSTRACT

A medical device for delivering a medicament to a patient. The device includes a syringe barrel assembly having a syringe barrel with a plunger movably insertable therein to expel medicament in the barrel. A needle cannula is connected to a needle cannula hub which is slidably arranged in the barrel for moving between an initial position in which the forward tip is exposed and a retracted position in which the forward tip is contained within the barrel. A retainer engages an annular groove defined in an inner surface of the barrel and secures the needle cannula hub at the initial position proximate the front end of the barrel. An urging member is arranged between the front end of the barrel and the needle cannula hub for urging the needle cannula hub toward the retracted position. The retainer is released in response to the application of medicament delivery force when the stopper is in a fully inserted position.

41 Claims, 7 Drawing Sheets

U.S. PATENT DOCUMENTS

| | | | |
|---|---|---|---|
| 5,308,332 A | 5/1994 | Dillard, III | |
| 5,312,372 A | 5/1994 | DeHarde et al. | |
| 5,336,176 A | 8/1994 | Yoon | |
| 5,342,309 A | 8/1994 | Hausser | |
| 5,342,310 A * | 8/1994 | Ueyama et al. | 604/110 |
| 5,342,320 A | 8/1994 | Cameron | |
| 5,370,628 A | 12/1994 | Allison | |
| 5,385,555 A | 1/1995 | Hausser | |
| 5,389,085 A | 2/1995 | D'Alessio | |
| 5,417,660 A | 5/1995 | Martin | |
| 5,562,626 A | 10/1996 | Sanpietro | |
| 5,651,774 A | 7/1997 | Taranto | |
| 5,658,254 A | 8/1997 | Reichenbach | |
| 5,681,292 A | 10/1997 | Tober | |
| 5,713,871 A | 2/1998 | Stock | |
| 5,735,823 A | 4/1998 | Berger | |
| 5,769,822 A | 6/1998 | McGary | |
| 5,800,395 A | 9/1998 | Botich | |
| 5,800,403 A | 9/1998 | Pressly | |
| 5,882,342 A | 3/1999 | Cooper | |
| 6,017,329 A | 1/2000 | Hake | |
| 6,077,253 A | 6/2000 | Cosme | |
| 6,162,197 A | 12/2000 | Mohammad | |
| 6,228,054 B1 | 5/2001 | Dysarz | |
| 6,319,233 B1 | 11/2001 | Jansen | |
| 6,432,087 B1 | 8/2002 | Hoeck et al. | |
| 6,432,088 B1 | 8/2002 | Huang et al. | |
| 6,440,104 B1 | 8/2002 | Newby et al. | |
| 6,443,929 B1 | 9/2002 | Kuracina | |
| 6,458,101 B1 | 10/2002 | Hu | |
| 6,458,105 B1 | 10/2002 | Rippstein et al. | |
| 6,461,333 B1 | 10/2002 | Frezza | |
| 6,461,362 B1 | 10/2002 | Halseth | |
| 6,475,194 B2 | 11/2002 | Domici, Jr. | |
| 6,478,780 B1 | 11/2002 | Shields | |
| 6,494,863 B1 | 12/2002 | Shaw | |
| 6,511,460 B1 | 1/2003 | Arnissolle | |
| 6,514,229 B1 | 2/2003 | Huang | |
| 6,527,742 B1 | 3/2003 | Malenchek | |
| 6,530,903 B2 | 3/2003 | Wang | |
| 6,547,762 B1 | 4/2003 | Botich | |
| 6,558,357 B1 | 5/2003 | Hoeck | |
| 6,565,540 B1 | 5/2003 | Perouse | |
| 6,569,115 B1 | 5/2003 | Barker | |
| 6,569,124 B1 | 5/2003 | Perouse | |
| 6,589,209 B1 | 7/2003 | Dysarz | |
| 6,595,954 B1 | 7/2003 | Luther | |
| 6,605,073 B1 * | 8/2003 | Pressly et al. | 604/506 |
| 6,712,787 B1 * | 3/2004 | Dysarz | 604/110 |
| 6,743,199 B2 * | 6/2004 | Shue et al. | 604/110 |
| 2002/0065488 A1 | 5/2002 | Suzuki et al. | |
| 2002/0193737 A1 | 12/2002 | Popovsky | |
| 2002/0193746 A1 | 12/2002 | Chevallier | |
| 2002/0193747 A1 | 12/2002 | Denolly | |
| 2003/0023205 A1 | 1/2003 | Botich | |
| 2003/0028171 A1 | 2/2003 | DeHarade | |
| 2003/0036730 A1 | 2/2003 | Teichert | |
| 2003/0050601 A1 | 3/2003 | Righi | |
| 2003/0050607 A1 | 3/2003 | Gaagnieux | |
| 2003/0078546 A1 | 4/2003 | Jensen | |
| 2003/0083627 A1 | 5/2003 | Chen | |
| 2003/0114799 A1 | 6/2003 | Cheikh | |
| 2003/0144630 A1 | 7/2003 | Chang | |
| 2003/0149403 A1 | 8/2003 | Barker | |
| 2003/0149404 A1 | 8/2003 | Lehmann | |

FOREIGN PATENT DOCUMENTS

| | | |
|---|---|---|
| EP | 0 680 767 A1 | 11/1995 |
| EP | 0 864 335 A2 | 9/1996 |
| EP | 0 740 942 A1 | 11/1996 |
| EP | 0 966 983 A1 | 12/1999 |
| EP | 1 258 263 A1 | 11/2002 |
| EP | 1 260 242 A1 | 11/2002 |
| EP | 0 901 391 B1 | 1/2003 |
| EP | 0 963 213 B1 | 1/2003 |
| EP | 1 273 316 A1 | 1/2003 |
| EP | 1 281 410 A1 | 2/2003 |
| EP | 0 916 354 B1 | 3/2003 |
| EP | 1 287 842 A1 | 3/2003 |
| EP | 1 291 029 A1 | 3/2003 |
| EP | 1 291 030 A1 | 3/2003 |
| EP | 1 317 938 A1 | 6/2003 |
| EP | 0 984 804 B1 | 7/2003 |
| EP | 1 329 234 A2 | 7/2003 |
| EP | 0 941 134 B1 | 8/2003 |
| EP | 1 205 173 A2 | 9/2003 |
| EP | 1 205 173 A3 | 9/2003 |
| EP | 0 734 738 B1 | 10/2003 |
| EP | 1 049 503 B1 | 10/2003 |
| FR | 2 830 764 A1 | 4/2003 |
| FR | 2 830 765 A1 | 4/2003 |
| GB | 2 282 069 A | 3/1995 |
| JP | 2001193714 | 12/2002 |
| WO | WO 01/41841 A2 | 6/2001 |
| WO | WO 01/41841 A3 | 6/2001 |
| WO | WO 01/60435 A1 | 8/2001 |
| WO | WO 01/85238 A2 | 11/2001 |
| WO | WO 02/089878 A1 | 11/2002 |
| WO | WO 02/098480 A2 | 12/2002 |
| WO | WO 02/098494 A2 | 12/2002 |
| WO | WO 02/098494 A3 | 12/2002 |
| WO | WO 03/000322 A1 | 1/2003 |
| WO | WO 03/000323 A1 | 1/2003 |
| WO | WO 03/011378 A1 | 2/2003 |
| WO | WO 03/015852 A1 | 2/2003 |
| WO | WO 03/022335 A2 | 3/2003 |
| WO | WO 03/033059 A1 | 4/2003 |
| WO | WO 03/033060 A1 | 4/2003 |
| WO | WO 03/041766 A2 | 5/2003 |
| WO | WO 03/045476 A1 | 6/2003 |
| WO | WO 03/045480 A1 | 6/2003 |
| WO | WO 03/045481 A1 | 6/2003 |
| WO | WO 03/063934 A1 | 8/2003 |
| WO | WO 03/068297 A1 | 8/2003 |
| WO | WO 03/068298 A1 | 8/2003 |

* cited by examiner

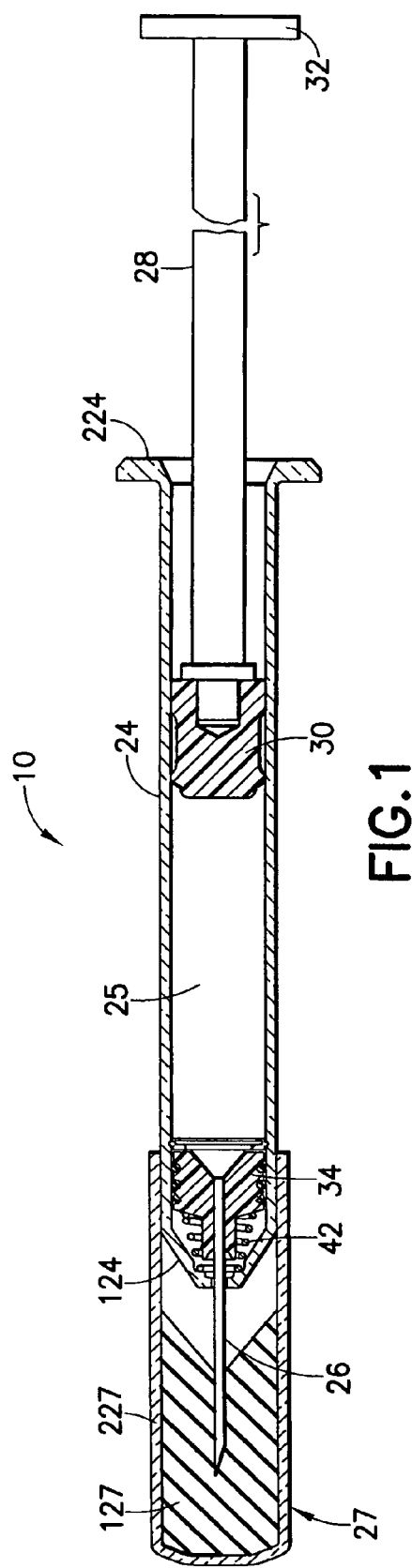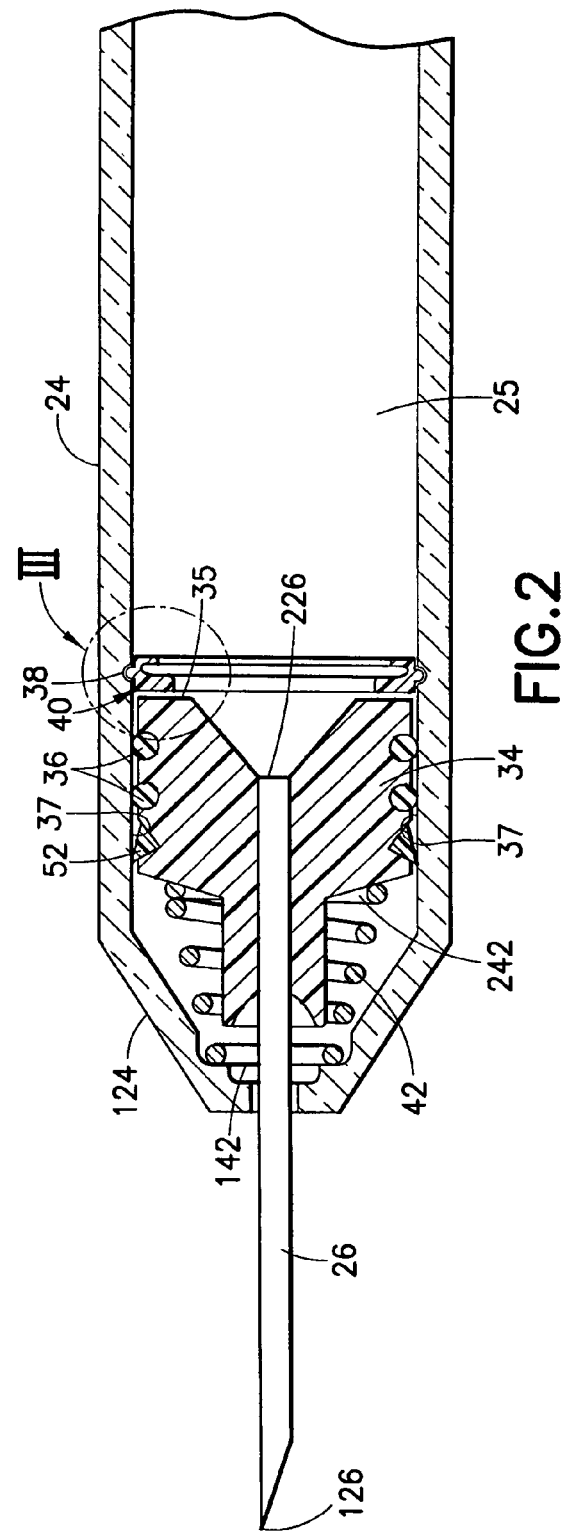

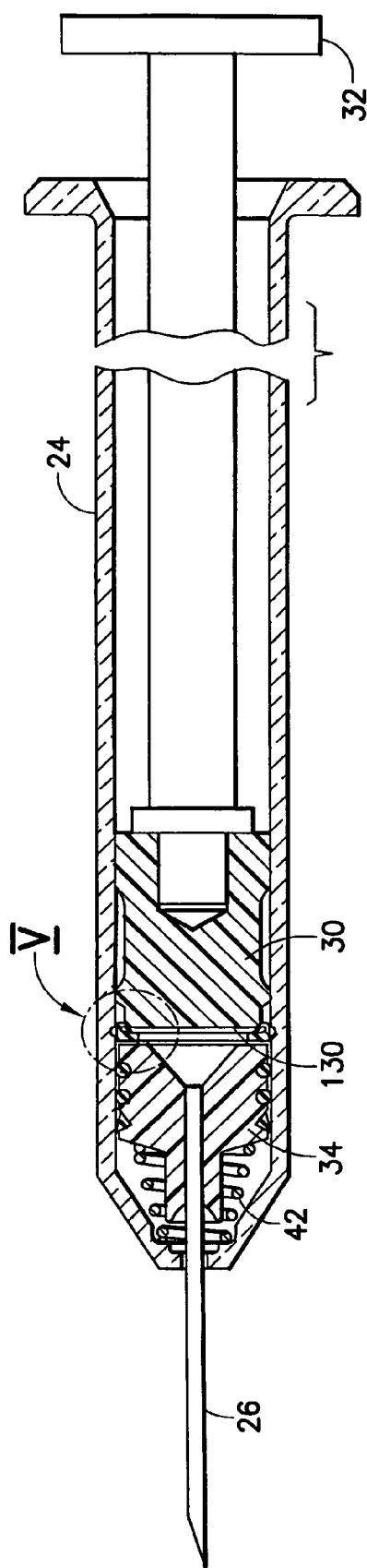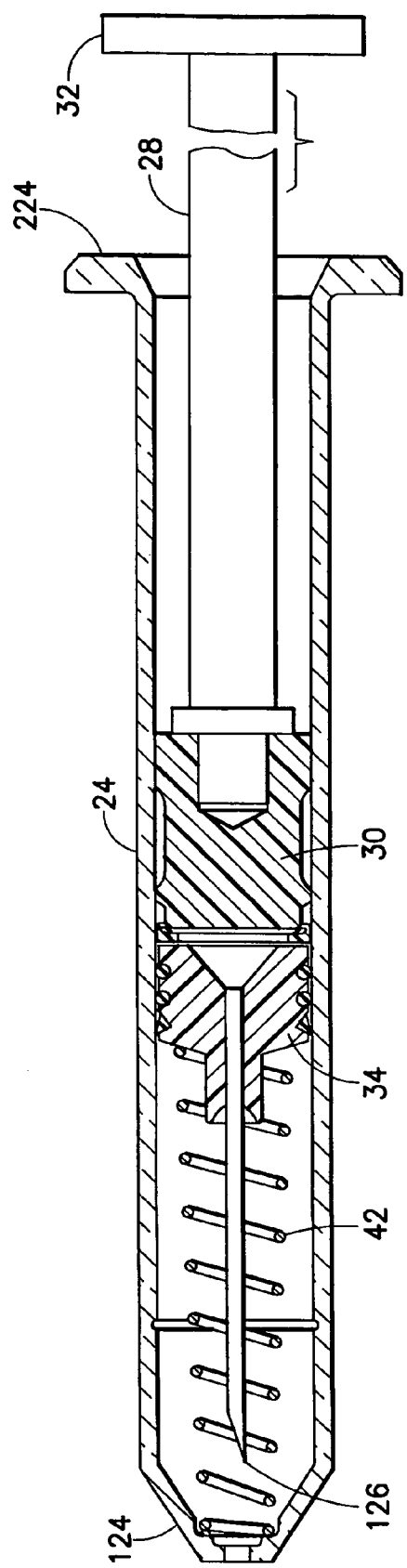

SYRINGE HAVING A RETRACTABLE NEEDLE

BACKGROUND OF THE INVENTION

1. Field of the Invention

The present invention relates to a medical device for delivering a dose of medicament by injection and having a mechanism for retracting the needle into the syringe after use for preventing accidental needle sticks after use.

2. Description of the Related Art

Syringes used for the delivery of medicaments to patients are well known. Oftentimes syringes are prefilled with a dosage of a medicament or other substance by a pharmaceutical manufacturer and then distributed to end users such as health care professionals or patients for administration of the prefilled medicament. Such syringes typically include a cylindrical hollow barrel which may be formed of a glass or plastic material and which includes the medicament. One end of the barrel is fitted with a fixed or removable hollow needle, and the other end of the barrel receives a plunger having a stopper which is slidable with respect to the barrel for delivery of the medicament to the hollow needle, i.e., to urge the medicament toward and out of the needle. A syringe assembly, which typically includes the above-described components, is usually stored with a removable needle cover which protects the needle from damage during storage and handling. Prior to use, the needle cover is removed to expose the needle.

To prevent a syringe user and, in particular, a health care professional from inadvertent sticks by the needle after use of the syringe on a patient, the syringe assembly may incorporate a safety shield which forms a guard to cover the needle after use. Certain attributes to be considered in such syringe assemblies are that the shield should be intuitive and easy to use, should preferably provide consistent and reliable activation, and should be operable with one hand. Other attributes are that such syringe assemblies require no change in current medicament delivery techniques, allow for dose adjustment, are preferably autoclavable, and allow for the inspection of contents before and after activation of the shield. Moreover, the use of the shield must not detrimentally affect processing and filling of the syringe at the pharmaceutical company, the assembly (i.e., syringe assembly and safety shield) must be easy to manufacture, must prevent accidental activation, and must limit the possibility of incurring cosmetic or structural damages.

SUMMARY OF THE INVENTION

The present invention relates to a medical device including a syringe barrel assembly with a retractable needle cannula supported by a needle cannula hub. The needle cannula and needle cannula hub are retracted after full delivery of the medicament dosage in the syringe.

A medical device for delivering a medicament to a patient according to the present invention includes a syringe barrel having a forward end and a rear end and defining a reservoir within which the medicament may be contained. A needle cannula having a forward tip and a rear end is connected to a needle cannula hub which is slidably arranged in the barrel at the forward end. The needle cannula hub is movable between an initial position in which forward tip of the needle cannula is exposed and a retracted position in which forward tip of the needle cannula is contained within the barrel. The rear end of said needle cannula is in fluid communication with the reservoir. A first end of a plunger with a stopper is positioned in the reservoir. A second end of the plunger has a thumb pad for receiving medicament delivery pressure for causing the plunger to move within the reservoir to cause the medicament to be expelled from the reservoir. A retainer engages an annular groove defined in an inner surface of the barrel and releasably secures the needle cannula hub at the initial position proximate the front end of the barrel. An urging member is arranged between the front end of the barrel and the needle cannula hub for urging the needle cannula hub toward the retracted position in the barrel. The retainer is released in response to the application of medicament delivery force to the plunger when the stopper is in a fully inserted position. Once the retainer is released and the medicament delivery pressure is removed from the thumb pad, an urgency of the urging member moves the needle cannula hub from the initial position to the retracted position, pushing back the stopper, which causes a slow retraction and prevents splatter from the needle. The splatter prevention allows for the user to be protected from blood born pathogens.

The retainer may be ring-shaped and have a radially outward projection engaging the groove defined in the barrel. The retainer further comprises a front part facing the forward end of the barrel and a rear part facing the rear end of the barrel. The rear part of the retainer interacts with one of the needle cannula hub and the stopper to release the radially outward projection from the groove when the stopper is moved to the fully inserted position.

In one embodiment, the retainer abuts a rear end of the needle cannula hub when the needle cannula hub is in the initial position. In this case, the stopper acts directly on the retainer to release the retainer.

In another embodiment, the retainer is arranged between the urging member and the needle cannula hub, thereby preventing an urgency of the urging member from acting on the needle cannula hub in the initial position. In this case, the needle cannula hub acts directly on the retainer to release the retainer.

The barrel may comprise a first section proximate the forward end having a first diameter and a second section having a second diameter, the first diameter being smaller than the second diameter. The needle cannula hub is arranged in the first section when in the initial position and is arranged in the second section when in the retracted position. Each of the first and second sections may be made of glass or plastic. Alternatively, one of the first and second sections may comprise plastic and the other of the first and second sections may comprise glass.

The needle cannula extends through a hole defined in the forward end of the barrel when the needle cannula hub is in the initial position and the needle cannula is contained within the barrel when the needle cannula is in the retracted position. In the embodiment in which the barrel includes a first section of a smaller diameter and a second section of a larger diameter, the needle cannula hub is forced askew by the urging member when the needle cannula hub is in the retracted position such that the forward tip of the needle cannula is not aligned with the forward end barrel hole when the needle cannula is in the retracted position. This prevents the needle cannula forward tip from being exposed from the barrel after use of the medical device.

A unidirectional ring may be arranged on the needle cannula hub for preventing movement of the needle cannula hub toward the forward end of the barrel and allowing movement of the needle cannula hub toward the rear end of the barrel.

The present invention also relates to a combination including a syringe barrel assembly and a retractable needle cannula assembly. The syringe barrel assembly includes a syringe barrel having a forward end and a rear end and defines a reservoir within which the medicament may be contained. A first end of a plunger has a stopper positioned in the reservoir and a second end of the plunger has a thumb pad for receiving medicament delivery pressure for causing the plunger to move within the reservoir to cause the medicament to be expelled from the reservoir.

The retractable needle cannula assembly includes a needle cannula having a forward tip and a rear end that is connected to a needle cannula hub which is slidably arranged in the barrel for moving between an initial position in which the forward tip is exposed and a retracted position in which the forward tip is contained within the barrel. The rear end of the needle cannula is in fluid communication with the reservoir. A retainer engages an annular groove defined in an inner surface of the barrel and releasably secures the needle cannula hub at the initial position proximate the front end of the barrel. An urging member arranged between the front end of the barrel and the needle cannula hub urges the needle cannula hub with the needle cannula toward the retracted position. The retainer is released in response to the application of medicament delivery force when the stopper is in a fully inserted position to enable the urging member to move the needle cannula hub from the initial position to the retracted position upon release of medicament delivery pressure from the thumb pad.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 1 is a longitudinal sectional view of a medical device according to an embodiment of the present invention;

FIG. 2 is an enlarged view of the front end of the medical device according to FIG. 1;

FIG. 4 is a longitudinal sectional view of the medical device of FIG. 1 after the medicament has been delivered;

FIG. 6 is a longitudinal sectional view of the medical device of FIG. 1 after the needle is moved to a retracted position;

DETAILED DESCRIPTION OF THE PRESENTLY PREFERRED EMBODIMENTS

Figure 3:
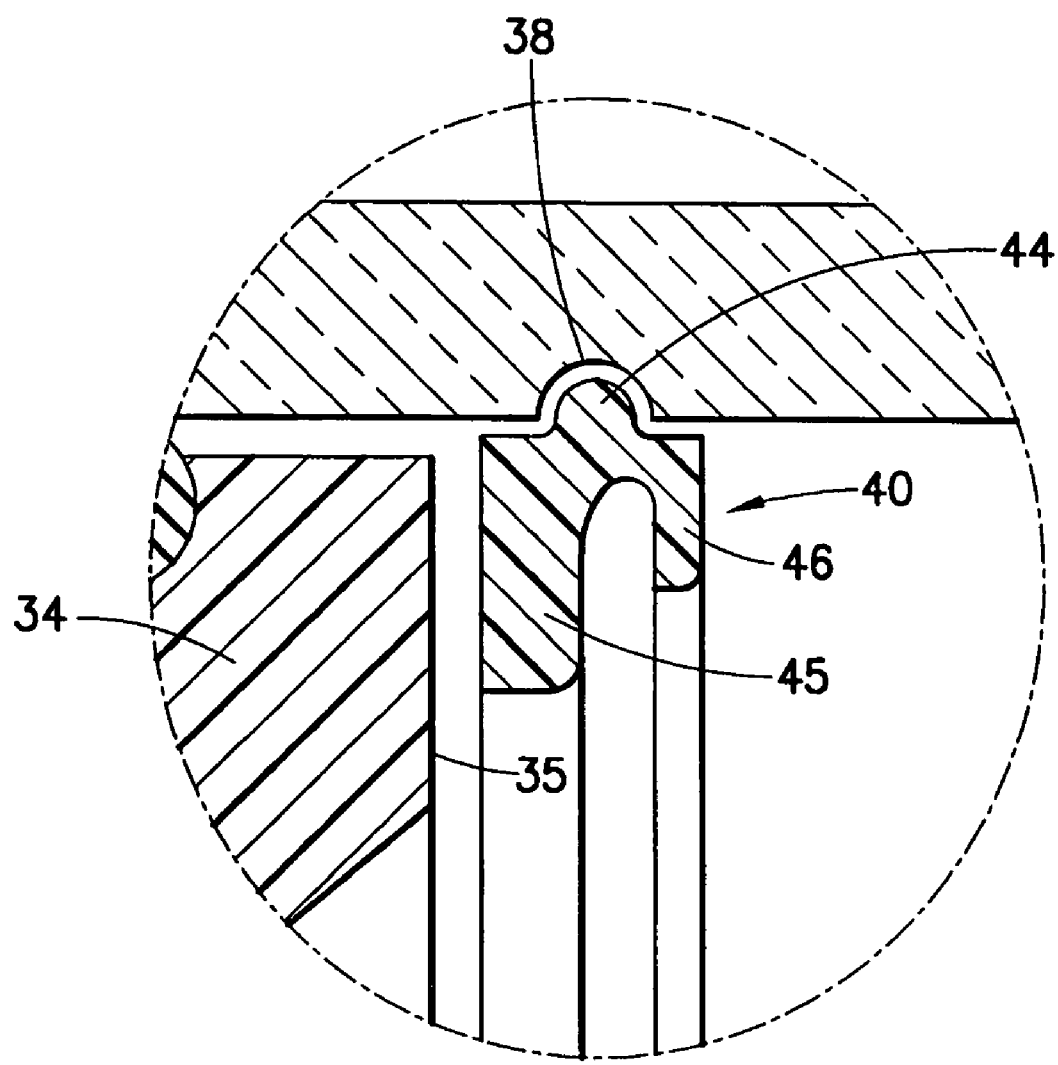
FIG. 3 is an enlarged sectional view of a retaining element of the medical device of FIG. 1.

FIGS. 1 and 2 show a medical device 10 for delivery of a medicament into a patient constructed in accordance with an embodiment of the present invention. As used herein the term "medicament" is intended to refer to any drug substance, vaccine, or other substance that is injected into a patient.

The medical device 10 is a syringe which includes a syringe barrel 24 having a front end 124 and a rear end 224. The barrel 24 is preferably made of molded plastic. Alternatively, the barrel 24 may be formed from glass. The barrel 24 defines a reservoir 25 within which the medicament may be held prior to the use of the medical device 10. A needle cannula 26 having a forward tip 126 and a rearward end 226 is connected in a needle cannula hub 34 proximate the front end 124 of the barrel 24. The needle cannula 26 is permanently connected to the needle cannula hub using an adhesive, glue, friction fit or other known or hereafter developed material or technique. The rear end 226 of the needle cannula is in fluid communication with the reservoir 25 in the position shown in FIGS. 1 and 2. The needle cannula hub 34 is arranged inside of the barrel 24 so that it is movable from an initial position shown in FIGS. 1 and 2 to a retracted position (described below) in which the forward tip 126 of the needle cannula 26 is contained within the barrel 24. One or more seals 36 may be arranged between the needle cannula hub 34 and an inner surface 37 of the barrel 24 to seal the reservoir 25 so that the only exposure of the medicament to the outside environment (e.g., to a patient, etc.) is through the needle cannula 26. Furthermore, a unidirectional retaining element such as a ring 52 is arranged on the needle cannula hub 34 which allows movement of the needle cannula hub 34 toward the retracted position but prohibits movement of the needle cannula hub 34 toward the front end 124 of the barrel 24. More specifically, when an attempt is made to move the needle cannula hub 34 forward, the portion of the ring 52 which contacts the inner side of the barrel 24 grips the inner side of the barrel 24 and is forced radially outward. This prevents forward movement of the needle cannula hub 34 within the barrel. However, when the needle cannula hub 34 is moved toward the rear of the barrel 24, the ring 52 slides on the inner surface of the barrel 24.

A plunger rod 28 has a first end inserted into the barrel 24 with a stopper or piston 30 arranged on the first end that is movable with the plunger rod 28 within the barrel 24. A second end of the plunger rod 28 includes a thumb pad 32 used for receiving pressure from the user's thumb for moving the piston 30 into and within the barrel 24. As further shown in FIG. 1, a removable needle shield 27 is disposed over the needle cannula 26 on the front end 124 of the barrel 24 to protect the needle from damage during handling of the medical device prior to its intended use. As is known, the needle shield may include a pliable part 127 and a rigid part 227.

As most clearly shown in FIG. 2, an urging member 42, such as, for example, a coil spring or biasing arm, is arranged between the needle cannula hub 34 and an inner surface of the front end 124 of the barrel 24 for urging the needle cannula hub 34 toward the rear end 224 of the barrel 24. As shown in FIG. 2, the spring 42 is preferably a tapered coil spring with a forward end 142 having a smaller diameter than a rearward end 242. In the initial position shown in FIGS. 1 and 2, the spring 42 is charged or compressed and biases the needle cannula hub 34 toward the rear end 224 of the barrel 24. A retaining element 40 arranged in an annular groove 38 formed in the inner surface of the barrel 24 holds or retains the needle cannula hub 34 in the initial position against the urgency of the spring 42. The retaining element 40 is preferably a ring-shaped element with a cross-section as shown in FIG. 3. A radial projection 44 of retaining element 40 engages the annular groove 38. A first leg 45 of the retaining element 40 faces the needle cannula hub 34 and a second leg 46 of the retaining element 40 faces the reservoir 25. In the initial position of the medical device 10 shown in FIGS. 1 and 2, a rear surface 35 of the needle cannula hub 34 abuts the first leg 45. The engagement between the radial projection 44 and the groove 38 maintains the needle cannula hub 34 in the initial position against the urgency of the spring 42.

Figure 5:
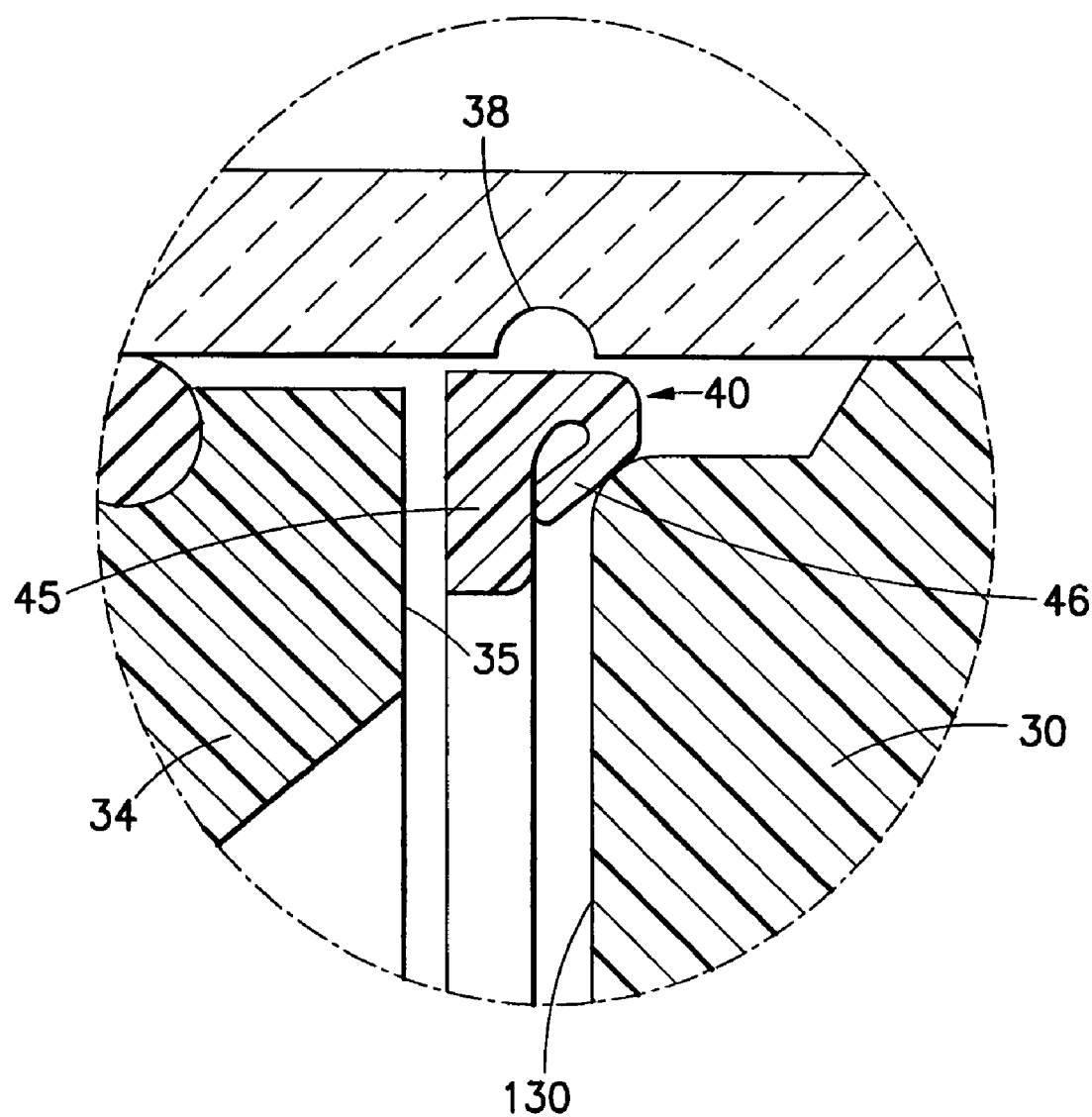
FIG. 5 is an enlarged sectional view of the retaining element in the state shown in FIG. 4.

FIG. 4 shows the position of the medical device 10 after the medicament has been fully delivered. In this position, the plunger rod 28 is fully inserted in the barrel 24 and a front face 130 of the piston 30 abuts the second leg 46 of the retaining element 40. When the plunger 28 is further inserted, the retaining element 40 deforms and the radial projection 44 disengages from the annular groove 38 as shown in FIG. 5. After the radial projection 44 is disengaged from the annular groove 38 and while medicament delivery pressure is still applied to the plunger 28, the spring 42 presses the retaining element 40 between the needle cannula hub 34 and the piston 30.

Since the retaining element 40 is disengaged by moving the piston 30 forward, the retaining element 40 may be located forward of the groove 38 when it is first disengaged. Accordingly, the retaining element 40 must be maintained in the deformed state as shown in FIG. 5 at least until it moves past the groove 38 toward the rear end of the barrel 24 so that the retaining element 40 does not reengage the groove 38. To accomplish this, the urgency of the spring 42 may be made sufficiently strong to clamp the retaining element 40 between the piston 30 and the needle cannula hub 34 and maintain the deformed state of the retaining element. Alternatively, the retaining element 40 may be made of a material that is permanently deformable such that once the retaining element 40 is deformed into the shape shown in FIG. 5, it remains deformed and does not reengage the groove 38.

When medicament delivery pressure is released from the thumb pad 32 of the plunger 28, the urgency of the spring 42 moves the needle cannula hub 34, the retaining element 40, the piston 30, and the plunger 28 toward the rear end 224 of the barrel 24 to the retracted position shown in FIG. 6 in which the front tip 126 of the needle is contained in the barrel 24. The movement is slow due to the fact that the stopper 30 and the needle cannula hub 34 must slide on the inner surface 27 of the barrel 24. After the needle cannula hub 34 is in the retracted position, the needle cannula hub 34 is held in the retracted position by the unidirectional ring 52 and the medical device 10 may be safely carried to and disposed in a sharps container.

Figure 7:
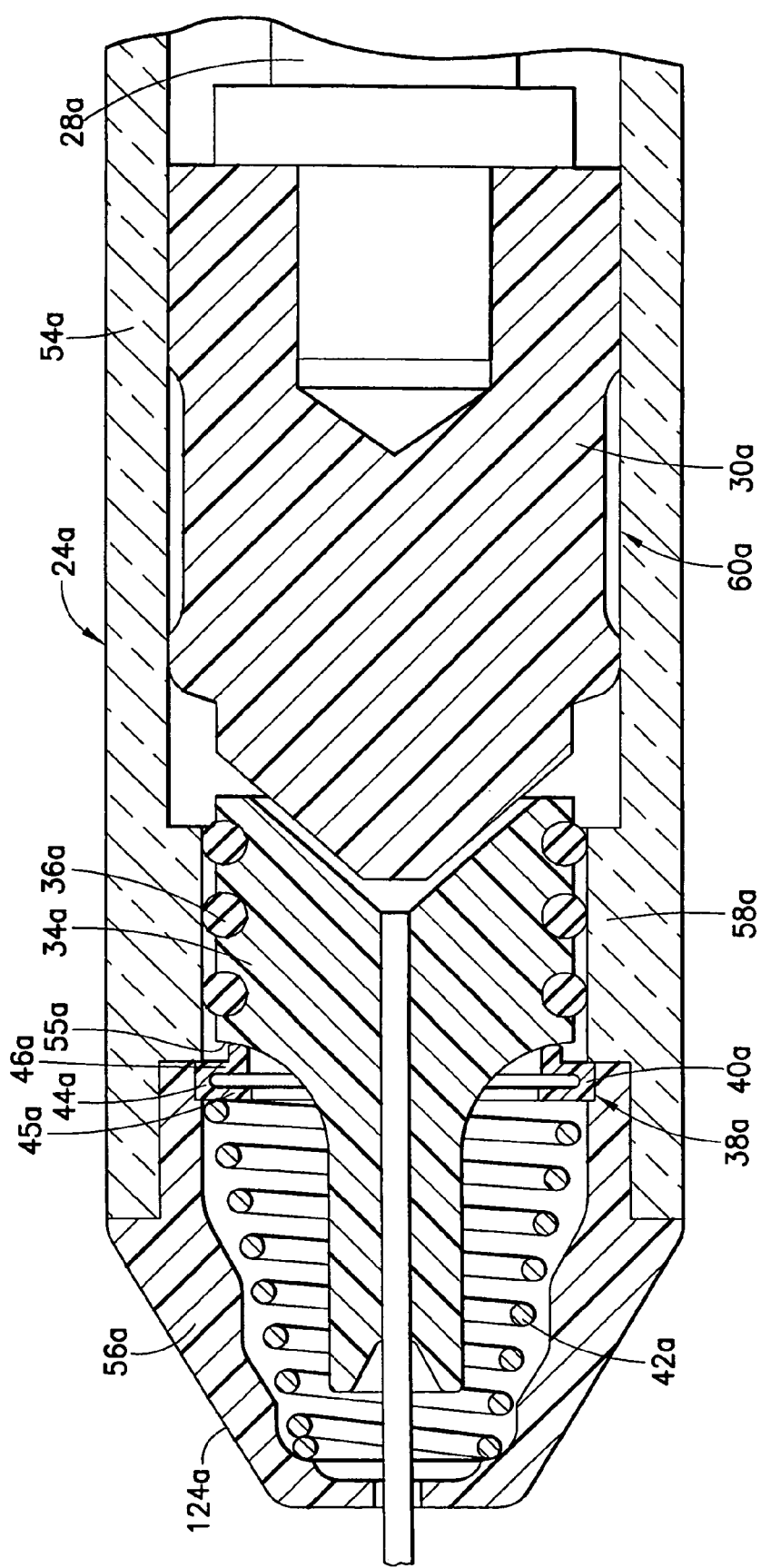
FIG. 7 is a partial sectional view of a further embodiment of a medical device according to the present invention.

FIG. 7 shows an alternate embodiment in which elements similar to the previous embodiments are labeled by the same reference characters and include a suffix 'a'. The barrel 24a comprises a first part 54a connected to a second part 56a. The connection of the first and second parts 54a, 56a may be made by adhesive, gluing, snap-fitting, press fitting, spin welding, heat stake, threading, or using other known or hereafter developed materials or techniques. The connection between the first and second parts 54a, 56a forms an annular groove 38a in which the retaining element 40a is engaged. In this embodiment, the retaining element 40a is arranged between the needle cannula hub 34a and the urging member 42a. The retaining element 40a includes first and second legs 45a, 46a and a radial projection 44a that engages that groove 38a. The first leg 45a abuts the urging member 42a and the second leg 46a abuts a front facing surface 55a of the needle cannula hub 34a. The seals 36a may be designed so that they are sufficient to hold the needle cannula hub 34a in the initial position. Alternatively, the retaining element 40a may be connected to or comprise an integral part of the needle cannula hub 34a such that the engagement of the retaining element 40a and the annular groove 38a holds the needle cannula hub 34a in the initial position and prevents the urgency of the urging member 42a from acting on the needle cannula hub 34a.

Figure 8:
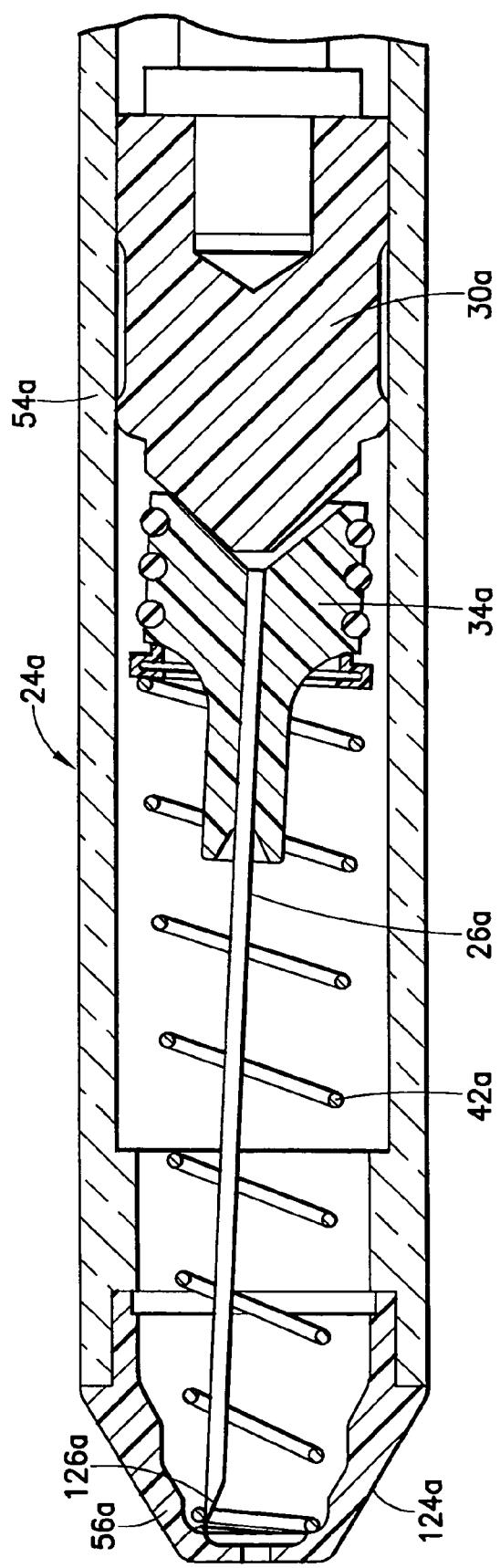
FIG. 8 is a partial sectional view of the medical device of FIG. 7 in the retracted position.

In the embodiment of FIG. 7, the needle cannula hub 34a is sealed in the first part 54a of the barrel 24a. A front section 58a of the first part 54a has a diameter, and a rear portion 60a of the first part 54a has an inner diameter which is different, and preferably larger than, the diameter of the front section 58a. After the plunger 28a is fully inserted and the medicament is fully delivered, the piston 30a contacts the rear end of the needle cannula hub 34a. To retract the needle 26a, the plunger 28a is first pushed further into the barrel 24a such that the needle cannula hub 34a is pushed forward and deforms the retaining element 40a until the retaining element 40a disengages from the annular groove 38a, similarly to the disengagement of the retaining element 40 shown in FIG. 5. Once the retaining element 40a is disengaged from the annular groove 38a, the retaining element 40a is clamped between the urging member 42a and the front surface 55a of the needle cannula hub 34 by the urgency of the urging member 42a. This maintains the retaining element 40a in the disengaged position. Once pressure is released from the thumb pad 32a of the plunger 28a, the urgency of the urging device 42a moves the needle cannula hub 34a, the piston 30a and the plunger 28a toward the retracted position. Once the needle cannula hub enters the rear portion 60a of the first part 54a of the barrel, the urging member 42a only has to overcome the resistance of the piston 30a against the side walls of the barrel 24a to push the needle cannula hub 34a to the retracted position. Furthermore, the unidirectional ring 52 is not required in this embodiment because the needle cannula hub 34a of this embodiment enters the larger diameter section of the first part of the barrel 24a in the retracted position. The urging member 42a exerts an uneven pressure such that the needle cannula hub 34a is held askew when it enters the larger diameter of the rear portion 60a as shown in FIG. 8. Accordingly, when the needle cannula hub 34a enters the retracted position the needle tip 126 is held out of alignment with the hole through the front end 124a of the barrel 24a.

Figure 9:
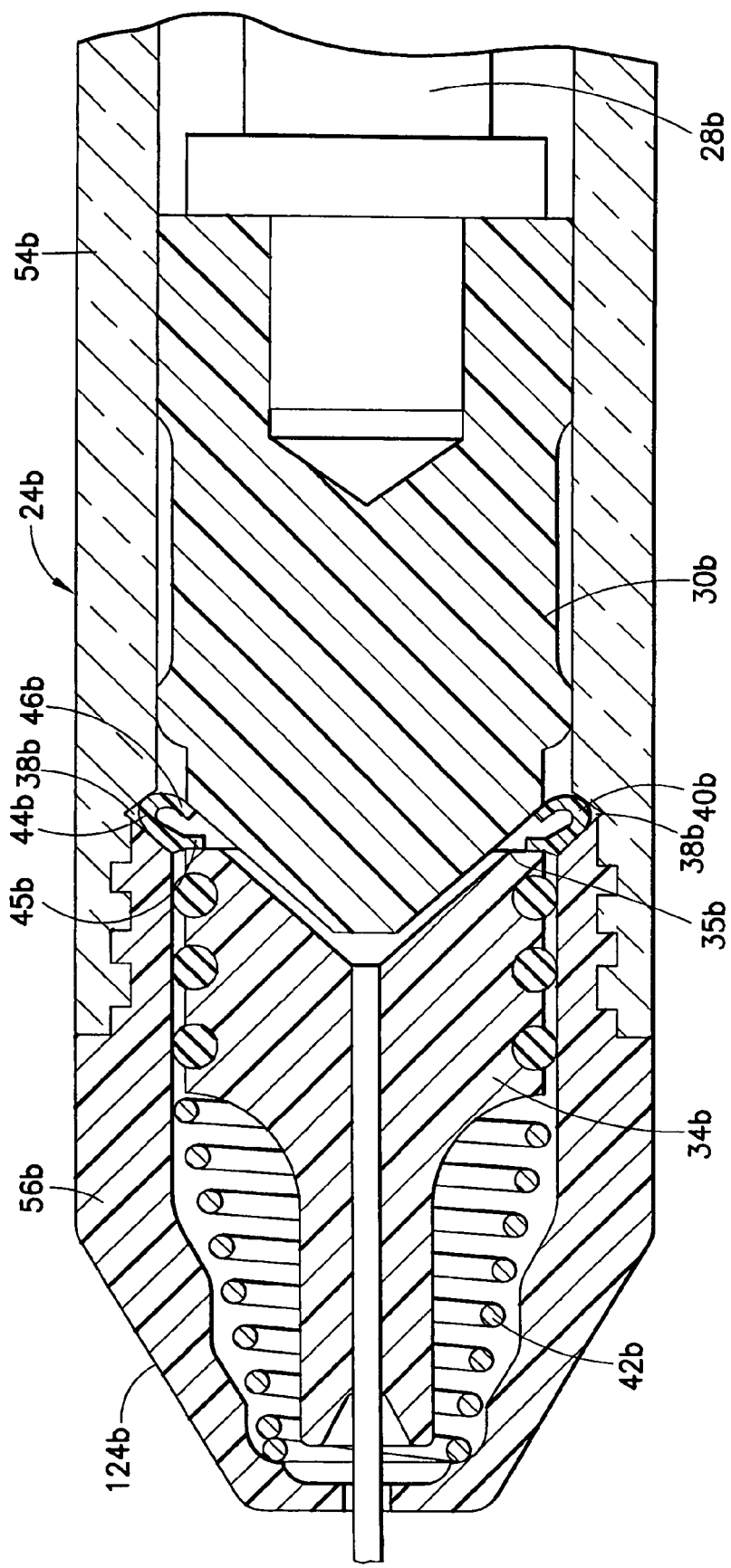
FIG. 9 is a partial sectional view of yet another embodiment of the medical device according to the present invention.

In the embodiment of FIG. 9, elements similar to the previous embodiments are labeled by the same reference characters and include a suffix 'b'. In FIG. 8, the barrel 24a is formed by first and second parts 54a, 56b, the second part 56b being arranged proximate the front end 124a of the barrel 24a. The connection of the first and second parts 54a, 56b may be made by adhesive, gluing, snap-fitting, press fitting, spin welding, heat stake, threading, or using other known or hereafter developed materials or techniques. In this embodiment, the first part 54a has a first diameter and the second part 56b has a second diameter which is smaller than the first diameter. A groove 38b is formed between the first and second parts 54a, 56b. The needle cannula hub 34a is movably arranged in the second part 56b. The urging member 42b is arranged between the second part 56b and the needle cannula hub 34a for urging the needle cannula hub 34a rearward as in the previous embodiments. A retaining element 40b is arranged in the annular groove 38b such that the rear facing surface 35b of the needle cannula hub 34a abuts the retaining element 40b and is thereby maintained in the initial position. As in the embodiment of FIGS. 1-6, the piston 30b interacts with the retaining element 40b after the medicament is fully delivered to release the retaining element 40b and allow the urging member 42b to move the needle cannula hub 34a to the retracted position in which the needle tip is contained in the barrel.

A description of an exemplary usage of the embodiment of the medical device 10 shown in FIGS. 1-6 will now be provided. It should be understood by a person of ordinary skill in the art that the following description is provided as an illustrative and non-limiting example. The health care professional receives the inventive medical device 10 pre-filled with a desired single dosage of a medicament. Immediately prior to use, the needle shield 27 is removed and the needle cannula 26 (with the forward tip 126) is exposed. The air can then be cleared from the barrel, and the dosage can be set. The health care professional pierces the patient's skin with the forward tip 126 of the needle cannula 26 and depresses the thumb pad 32 to cause the plunger rod 28 and stopper 30 or piston to move within the reservoir 25. As the plunger 28 and piston are moved into the reservoir, medicament is caused to be expelled from the reservoir, through the needle cannula 26, and into the patient. When the medicament is completely expelled from the reservoir so that the dose has been completely administered to a patient, the stopper 30 (or the needle cannula hub 34 in the embodiments of FIGS. 7-9) interacts with retainer 40, as described in detail above, thereby releasing the retainer 40 and allowing the needle cannula hub 34 to move from the initial position to the retracted position under the force of the spring or urging member 42. When in the retracted position, the forward tip 126 of the needle cannula 26 is completely contained within the syringe barrel 24 at a distance for preventing the forward tip 126 from coming in contact with the tip of a user's finger. The used medical device 10 may then be disposed of in a suitable sharps disposal container.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A medical device for delivering a medicament to a patient, comprising:
   a syringe barrel having a forward end and a rear end and defining a reservoir within which the medicament may be contained;
   a needle cannula having a forward tip and a rear end and being connected to a needle cannula hub movable in said barrel between an initial position in which said forward tip is exposed and a retracted position in which said forward tip is contained within said barrel, said rear end of said needle cannula being in fluid communication with said reservoir through said needle cannula;
   a plunger having a first end with a stopper positionable in said reservoir and a second end having a thumb pad for receiving medicament delivery pressure for causing said plunger to move within said reservoir to cause the medicament to be expelled from said reservoir;
   a retainer engaging an annular groove defined in an inner surface of said barrel and releasably securing said needle cannula hub at said initial position proximate the front end of said barrel, said retainer being ring-shaped and having a cross-sectional shape with a radially outward projection engaging the groove defined in said barrel, a first leg facing said forward end of said barrel, and a second leg facing said rear end of said barrel; and
   an urging member arranged between said front end of said barrel and said needle cannula hub and having an urgency for urging said needle cannula hub with said needle cannula toward the retracted position in said barrel, said second leg interacting with one of said needle cannula hub and said stopper to release said radially outward projection from said groove in response to the application of medicament delivery force to said thumb pad when said stopper is in a fully inserted position in said reservoir to allow said urging member to move said needle cannula hub from said initial position to said retracted position upon release of medicament delivery pressure from said thumb pad.

2. The medical device of claim 1, wherein said barrel comprises a first section proximate said forward end having a first diameter and a second section having a second diameter, said first diameter being different than said second diameter.

3. The medical device of claim 2, wherein said needle cannula hub is arranged in said first section in the initial position and is arranged in said second section in the retracted position.

4. The medical device of claim 3, wherein said barrel comprises a first part connected to a second part, said first part defining at least a portion of said first section and said second part defining said second section.

5. The medical device of claim 4, wherein both said first and second sections comprise glass.

6. The medical device of claim 4, wherein both said first and second sections comprise plastic.

7. The medical device of claim 4, wherein one of said first and second sections comprises plastic and the other of said first and second sections comprises glass.

8. The medical device of claim 4, wherein each of said first and second parts define a portion of said annular groove in which said retainer is engaged when said needle cannula hub is in said initial position.

9. The medical device of claim 4, wherein said first part defines the entire first section.

10. The medical device of claim 3, wherein said needle cannula extends through a hole defined in said forward end of said barrel when the needle cannula hub is in the initial position and said needle cannula hub is forced askew by said urging member when the needle cannula hub is in said retracted position such that the forward tip of the needle cannula is not aligned with said hole in said retracted position.

11. The medical device of claim 1, wherein said first leg of said retainer abuts a rear end of said needle cannula hub when said needle cannula hub is in said initial position.

12. The medical device of claim 11, wherein said stopper acts directly on said second leg of said retainer to deform said second leg and release said retainer.

13. The medical device of claim 1, wherein said retainer is arranged between said urging member and said needle cannula hub, thereby preventing an urgency of said urging member from acting on said needle cannula hub in the initial position.

14. The medical device of claim 13, wherein said needle cannula hub acts directly on said second leg of said retainer to deform said second leg and release said retainer.

15. The medical device of claim 1, wherein said urging member is a coil spring.

16. The medical device of claim 15, wherein said coil spring is a tapered coil spring.

17. The medical device of claim 1, further comprising a unidirectional ring arranged between said needle cannula and said inner surface of said barrel preventing movement of said needle cannula hub toward said forward end of said barrel and allowing movement of said needle cannula hub toward said rear end of said barrel.

18. The medical device of claim 1, wherein said barrel comprises a plastic material.

19. The medical device of claim 1, wherein said urging member moves said retaining element and said plunger along with said needle cannula hub in said barrel to said retracted position when said retainer is released from engagement with said annular groove and medicament delivery pressure is released from said thumb pad.

20. The medical device of claim 1, wherein said urgency of said urging member provides a clamping force to said retaining element when said retaining element is released from said annular groove to prevent reengagement of said retaining element in said annular groove.

21. The medical device of claim 1, wherein said retaining element is permanently deformable such that said retaining element remains disengaged from said annular groove after said retaining element is released from engagement with said annular groove.

22. The medical device of claim 1, wherein said first and second legs of said retaining element extend radially inward before interacting with one of said needle cannula hub and said stopper to release said radially outward projection.

23. A combination including a syringe barrel assembly and a retractable needle cannula assembly, said syringe barrel assembly comprising a syringe barrel having a forward end and a rear end and defining a reservoir within which the medicament may be contained, a plunger having a first end with a stopper positionable in said reservoir and a second end having a thumb pad for receiving medicament delivery pressure for causing said plunger to move within said reservoir to cause the medicament to the expelled from said reservoir; and said retractable needle cannula assembly comprising a needle cannula having a forward tip and a rear end and being connected to a needle cannula hub that is movable in said barrel for moving between an initial position in which said forward tip is exposed and a retracted position in which said forward tip is contained within said barrel, said rear end of said needle cannula being in fluid communication with said reservoir, a retainer engaging an annular groove defined in an inner surface of said barrel and releasably securing said needle cannula hub at said initial position proximate the front end of said barrel, said retainer being ring-shaped and having a cross-sectional shape with a radially outward projection engaging the groove defined in said barrel, a first leg facing said forward end of said barrel, and a second leg facing said rear end of said barrel, and an urging member arranged between said front end of said barrel and said needle cannula hub having an urgency for urging said needle cannula hub with said needle cannula toward said retracted position in said syringe barrel, said second leg interacting with one of said needle cannula hub and said stopper to release said radially outward projection from said groove in response to the application of medicament delivery force to said thumb pad when said stopper is in a fully inserted position in said reservoir to allow said urging member to move said needle cannula hub from the initial position to the retracted position upon release of medicament delivery pressure from said thumb pad.

24. The combination of claim 23, wherein said barrel comprises a first section proximate said forward end having a first diameter and a second section having a second diameter, said first diameter being different than said second diameter.

25. The combination of claim 24, wherein said needle cannula hub is arranged in said first section in the initial position and is arranged in said second section in the retracted position.

26. The combination of claim 25, wherein said barrel comprises a first part connected to a second part, said first part defining at least a portion of said first section and said second part defining said second section.

27. The combination of claim 26, wherein both said first and second sections comprise glass.

28. The combination of claim 26, wherein both said first and second sections comprise plastic.

29. The combination of claim 26, wherein one of said first and second sections comprises plastic and the other of said first and second sections comprises glass.

30. The combination of claim 26, wherein each of said first and second parts define a portion of said annular groove in which said retainer is engaged when said needle cannula hub is in said initial position.

31. The combination of claim 26, wherein said first part defines the entire first section.

32. The combination of claim 23, wherein said first leg of said retainer is arranged to abut a rear end of said needle cannula hub when said needle cannula hub is in said initial position.

33. The combination of claim 32, wherein said stopper acts directly on said second leg of said retainer to deform said second leg and release said retainer.

34. The combination of claim 23, wherein said retainer is arranged between said urging member and said needle cannula hub, thereby preventing an urgency of said urging member from acting on said needle cannula hub in the initial position.

35. The combination of claim 34, wherein said needle cannula hub acts directly on said second leg of said retainer to deform said second leg and release said retainer.

36. The combination of claim 23, wherein said syringe barrel comprises a plastic material.

37. The combination of claim 23, wherein said syringe barrel comprises a glass material.

38. The combination of claim 23, wherein said urging member moves said retaining element and said plunger along with said needle cannula hub in said barrel to said retracted position when said retainer is released from engagement with said annular groove and medicament delivery pressure is released from said thumb pad.

39. The combination of claim 23, wherein said urgency of said urging member provides a clamping force to said retaining element when said retaining element is released from said annular groove to prevent reengagement of said retaining element in said annular groove.

40. The combination of claim 23, wherein said retaining element is permanently deformable such that said retaining element remains disengaged from said annular groove after said retaining element is released from engagement with said annular groove.

41. The combination of claim 23, wherein said first and second legs of said retaining element extend radially inward before interacting with one of said needle cannula hub and said stopper to release said radially outward projection.

* * * * *